United States Patent

Ball et al.

Patent Number: 5,949,895
Date of Patent: *Sep. 7, 1999

[54] DISPOSABLE AUDIO PROCESSOR FOR USE WITH IMPLANTED HEARING DEVICES

[75] Inventors: Geoffrey R. Ball, Sunnyvale; Bob H. Katz, Los Gatos; Bruce D. Arthur, San Jose, all of Calif.

[73] Assignee: Symphonix Devices, Inc., San Jose, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/526,129

[22] Filed: Sep. 7, 1995

[51] Int. Cl.6 ............................. H04R 25/00; A61M 1/18
[52] U.S. Cl. .......................... 381/326; 381/322; 600/25; 607/57
[58] Field of Search .................. 381/68.2, 68.4, 381/69, 312, 313, 314, 316, 322, 380, 381, 317, 326, 328, 68.3, 68; 600/25; 607/56, 57; 128/746

[56] References Cited

U.S. PATENT DOCUMENTS

| | | | |
|---|---|---|---|
| 3,571,529 | 3/1971 | Gharib | 381/322 |
| 4,334,315 | 6/1982 | Ono et al. | 381/315 |
| 4,352,960 | 10/1982 | Dormer et al. | 179/107 |
| 4,425,481 | 1/1984 | Mansgold et al. | 381/68 |
| 4,533,795 | 8/1985 | Baumhauer, Jr. et al. | 179/111 |
| 4,817,609 | 4/1989 | Perkins et al. | 128/420 |
| 4,850,023 | 7/1989 | Yarush | 381/67 |
| 4,882,762 | 11/1989 | Waldhamer | 381/106 |
| 5,015,224 | 5/1991 | Maniglia | 600/25 |
| 5,239,588 | 8/1993 | Davis | 381/68 |
| 5,282,858 | 2/1994 | Bisch | 600/25 |
| 5,289,544 | 2/1994 | Franklin | 381/68.1 |
| 5,298,692 | 3/1994 | Ikeda et al. | 381/135 |
| 5,303,306 | 4/1994 | Brillhart et al. | 381/68 |
| 5,319,717 | 6/1994 | Holesha | 381/168 |
| 5,321,758 | 6/1994 | Charpentier et al. | 381/68.2 |
| 5,327,499 | 7/1994 | Sohayda | 381/68 |
| 5,338,287 | 8/1994 | Miller et al. | 600/25 |
| 5,363,444 | 11/1994 | Norris | 379/430 |
| 5,395,168 | 3/1995 | Leenen | 381/68.6 |
| 5,568,516 | 10/1996 | Strohallen et al. | 381/163 |
| 5,606,621 | 2/1997 | Reiter et al. | 381/68.6 |
| 5,615,229 | 3/1997 | Sharma et al. | 381/79 |
| 5,812,598 | 9/1998 | Sharma et al. | 381/94.8 |

*Primary Examiner*—Curtis A. Kuntz
*Assistant Examiner*—Rexford N Barnie
*Attorney, Agent, or Firm*—Townsend and Townsend and Crew LLP

[57] ABSTRACT

A disposable audio processor for use with implanted hearing devices is provided. The audio processor may include a microphone, application specific integrated circuit performing both signal processing and signal modulation, a battery, and a coil. The audio processor is designed for specific types of hearing loss. Electronic signals are transmitted to an implanted receiver through the use of electromagnetic fields generated by the coil of the audio processor. The audio processor is a low power and inexpensive device that may be disposed of when it becomes inoperable. The audio processor and may include a finger tab for manipulating the device.

9 Claims, 8 Drawing Sheets

DISPOSABLE AUDIO PROCESSOR FOR USE WITH IMPLANTED HEARING DEVICES

BACKGROUND OF THE INVENTION

The present invention relates to the field of devices and methods for improving hearing in hearing impaired persons and, more particularly, to external audio processors for use with implanted hearing devices.

Traditional hearing aids have generally been devices including a microphone, an amplifier and a speaker placed in a person's external ear canal. The microphone picks up ambient sounds which the amplifier amplifies and delivers to the speaker (also known as the "receiver"). The speaker broadcasts the amplified sound at a much louder level to the hearing impaired person. Recently, hearing aid devices have incorporated advanced integrated circuit designs that shape the amplified sounds to best suit the person's hearing loss. Although there have been numerous advancements in traditional hearing aid devices, inherent problems still remain.

Traditional hearing aid devices have the inherent problem of occlusion. The electronic components of the hearing aid are housed in a plastic or acrylic ear plug which is placed in the external ear canal. Placing the hearing aid in the ear canal diminishes the hearing impaired person's natural ability to hear by occluding the ear canal. Thus, traditional hearing aid devices cause the user to rely almost solely upon the hearing aid and the resulting occlusion is thought to be at least partially responsible for complaints of unnatural or poor sounding devices.

Traditional hearing aid devices also have the inherent problem of feedback. Feedback commonly occurs when a microphone is placed in close proximity to an amplified speaker output. As the microphone and the amplified speaker output of a hearing aid are in close proximity, there is an omnipresent opportunity for a feedback loop to be established resulting in an extremely loud "whistle" or "squeal" being broadcast from the device. In order to minimize feedback, the microphone and speaker should be acoustically isolated from one another. However, acoustic isolation usually involves reducing the vent tube volume which in turn increases the opportunity for feedback.

Implanted hearing devices have been designed that reduce many of the problems attendant with traditional hearing aids. Implanted hearing devices typically include a mechanical mechanism that is implanted in the middle or inner ear to vibrate middle or inner ear structures. The mechanical mechanism is typically driven by electronic signals from an external audio processor. Examples of these hearing devices are described in U.S. Pat. No. 5,015,224, issued May 14, 1991 to Maniglia, U.S. Pat. No. 4,606,329, issued Aug. 19, 1986 to Hough, and U.S. Pat. No. 5,282,858, issued Feb. 1, 1994 to Bisch et al.

Implanted hearing devices alleviate many of the problems associated with traditional hearing aid devices including occlusion and feedback. However, conventional implanted hearing devices still share many problems with traditional hearing aids.

Hearing devices in general are high maintenance devices. Battery doors and contacts continuously wear out and must be replaced. Also, microphones should be kept clean to operate properly. As hearing devices can easily be damaged, high levels of physical exercise or activity can generate problems. For these reasons and others, hearing devices are frequently returned to a hearing device dispenser or audiologist for service or repair which lowers the availability of the hearing device and increases the maintenance cost.

Hearing devices are generally very expensive to initially obtain. As the hearing device is expensive, many users do not have spare hearing devices. Thus, when a hearing device becomes inoperable or lost, the user generally has to forego assisted hearing until the hearing device is serviced or a new one is obtained.

What is needed is a device that alleviates common problems associated with traditional hearing aids like occlusion and feedback, and also solves the problems of maintenance, availability and cost associated with hearing devices in general. The present invention fulfills these and other needs.

SUMMARY OF THE INVENTION

The present invention provides an innovative audio processor for use with implanted hearing devices. An audio processor of the present invention is a low cost, low power device that is manufactured in such a way that the audio processor is disposable when it becomes inoperable. The disposable audio processor achieves a reduced cost by providing a simplified signal processing scheme, simplified control(s) and lower manufacturing cost. The decrease in device power requirements produces a proportional increase in device longevity (up to one month and more). Also, the audio processor is small which reduces the likelihood of skin irritation. Therefore, a hearing impaired person is able to obtain a set of audio processors which are essentially maintenance free devices as an inoperable audio processor may be readily replaced with a fresh audio processor. The inoperable audio processor may then be disposed of or recycled.

The simplified signal processing scheme is implemented in a monolithic application specific integrated circuit. Monolithic integration of the audio processor function provides a device that is less expensive to build, test and package. It further provides a reduction in power consumption for a given set of processing requirements. The application specific nature of the signal processing is such that audio processors are tailored for particular categories of hearing losses including the following: flat (relatively constant hearing deficiency), sloping (hearing deficiency that is relatively proportional or inversely proportional to frequency) and cookie bite (hearing deficiency of midrange frequencies). By providing processors specific to hearing loss categories or individual users, the need for programmable devices with multiple controls for adjusting signal processing responses is eliminated, thereby reducing manufacturing costs.

The present invention provides a method of providing hearing assistance to hearing impaired persons including the steps of providing a plurality of external audio processors for use with an implanted hearing device, each of the audio processors specifically designed for a particular category of hearing loss; and selecting an external audio processor to suit a hearing impaired person. In a preferred embodiment, the hearing impaired person is provided a set of disposable audio processors so that a new audio processor may be activated when the one in use becomes inoperable.

An audio processor of the present invention typically includes a low cost microphone, an application specific integrated circuit performing both signal processing and signal modulation, a battery and a coil to transcutaneously transmit the processed signal to an implantable hearing device. The audio processor is maintained against the skin by the use of magnets or adhesive. In a preferred embodiment, the audio processor components are mounted on an inexpensive printed circuit board and coated with a low cost epoxy or polymer mold material that is generally impervious to moisture and which imparts mechanical strength and protection to the electronics. Also, the audio processor may include a tab to aid the user in manipulating the audio processor.

Further, aspects and advantages of the present invention will become readily apparent upon a perusal of the following description in reference to the accompanying drawings.

DESCRIPTION OF THE PREFERRED EMBODIMENT

In a preferred embodiment, the audio processor of the present invention is utilized in conjunction with a floating mass transducer hearing device. The floating mass transducer is described in complete detail in U.S. patent application Ser. No. 08/368,219, entitled "IMPLANTABLE AND EXTERNAL HEARING SYSTEMS HAVING A FLOATING MASS TRANSDUCER," filed Jan. 3, 1995 by Geoffrey R. Ball et al., which is hereby incorporated by reference for all purposes. The floating mass transducer is typically attached to one of the vibrating structures (e.g., ossicles) in the middle or inner ear. The floating mass transducer is a highly efficient device which allows the audio processor to operate at extremely low power levels. Low power levels in turn allow the audio processor of the present invention to be smaller and manufactured at a substantially lower cost. Although the present invention is preferably utilized with the floating mass transducer, the present invention may be utilized with other implantable hearing devices.

Figure 1:
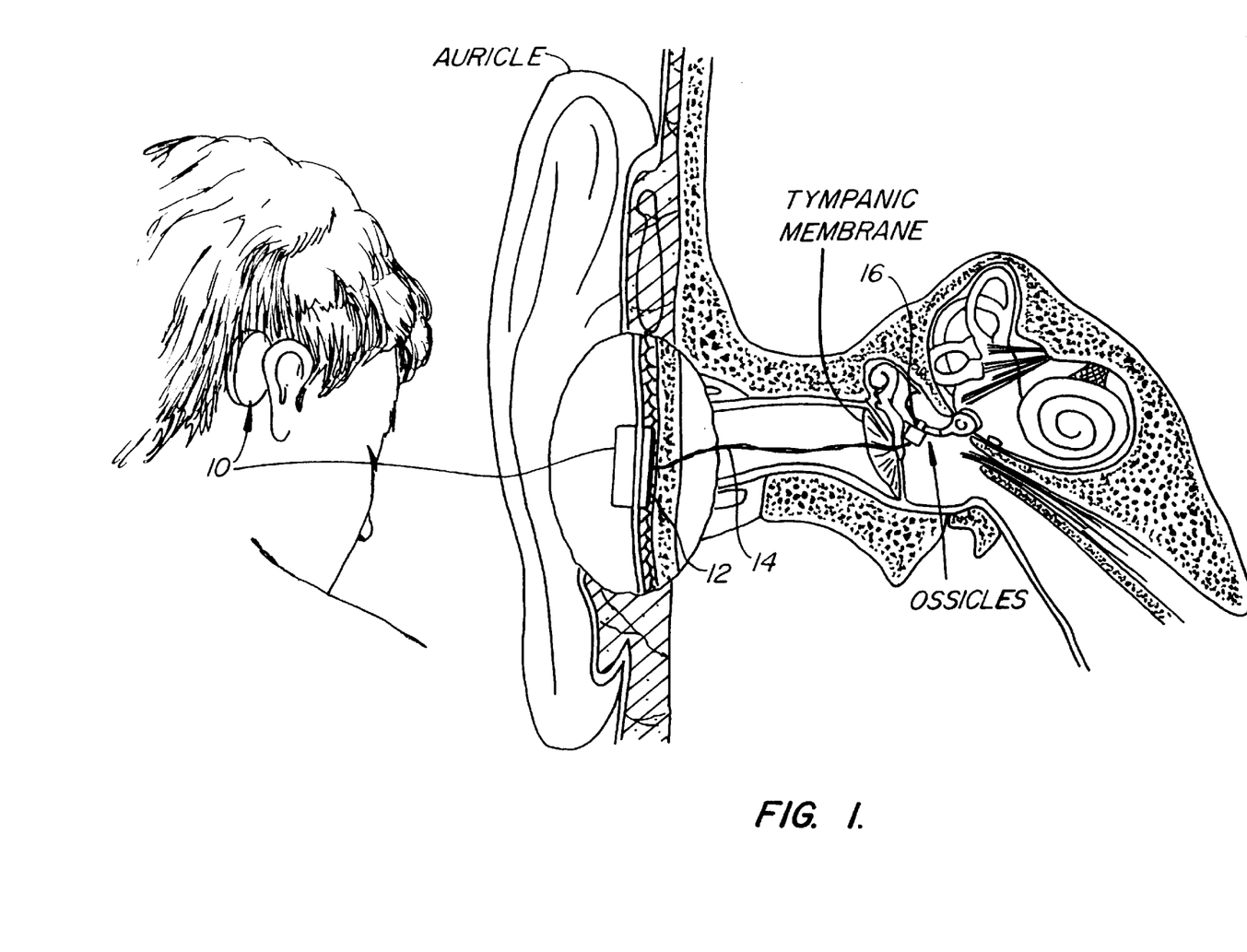
FIG. 1 shows a cross-sectional view of an audio processor of the present invention in a post auricle location.

FIG. 1 shows a cross-sectional view of a human ear with an audio processor of the present invention located in a post auricle location. An audio processor 10 is attached to the skin behind the auricle of a hearing impaired person. The audio processor receives, amplifies, and processes ambient sounds which are transmitted transcutaneously to a receiver 12. As will be described in more detail in the following paragraphs, the audio processor typically modulates the electronic signal corresponding to the amplified and/or processed ambient sounds and transmits a modulated signal to the receiver via electromagnetic fields generated by a coil. Receiver 12 includes a coil that transforms the electromagnetic field generated by the audio processor into an electronic signal. If the audio processor modulated the signal to reduce the likelihood of interference from external sources, receiver 12 also demodulates the corresponding electronic signal.

The receiver transmits the electronic signals over electrodes 14 to an implanted hearing device 16. The implanted hearing device is shown attached to an ossicle and in a preferred embodiment, the implanted hearing device is a floating mass transducer hearing device as described in U.S. patent application Ser. No. 08/368,219, previously incorporated by reference.

Figure 2:
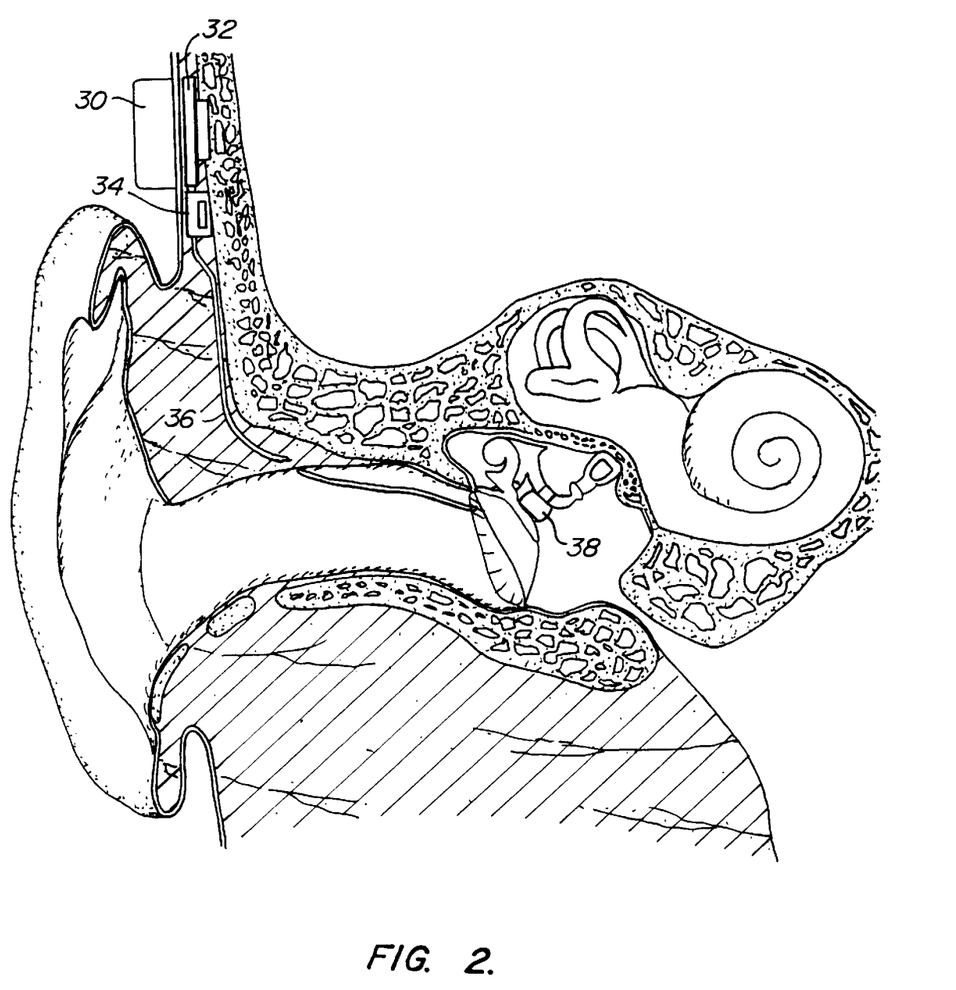
FIG. 2 shows a cross-sectional view of an audio processor placed above the auricle.

FIG. 2 shows a cross-sectional view of an audio processor attached above the auricle. An audio processor 30 receives ambient sounds, produces an amplified and/or processed electronic signal corresponding to the ambient sounds, and modulates the resulting electronic signal. The audio processor transmits the modulated electronic signal transcutaneously to a receiver 32 through the use of coils. The receiver transmits the amplified modulated signal to a demodulator 34. The demodulator demodulates the electronic signal from the receiver and transmits the demodulated electronic signals through electrodes 36 to an implanted hearing device 38.

The electrodes are electrically connected to demodulator 34 and pass through cartilage to near the ear canal where the electrodes travel under the skin of the ear canal to the tympanic membrane. At the tympanic membrane, the electrodes continue to pass under the skin into the middle ear so that the tympanic membrane is not pierced. This approach is referred to as the transcanal approach. Alternatively, a mastoidectomy may be performed where the electrodes pass through an excavated canal in the mastoid bone reaching the middle ear at the facial recess.

Figure 3:
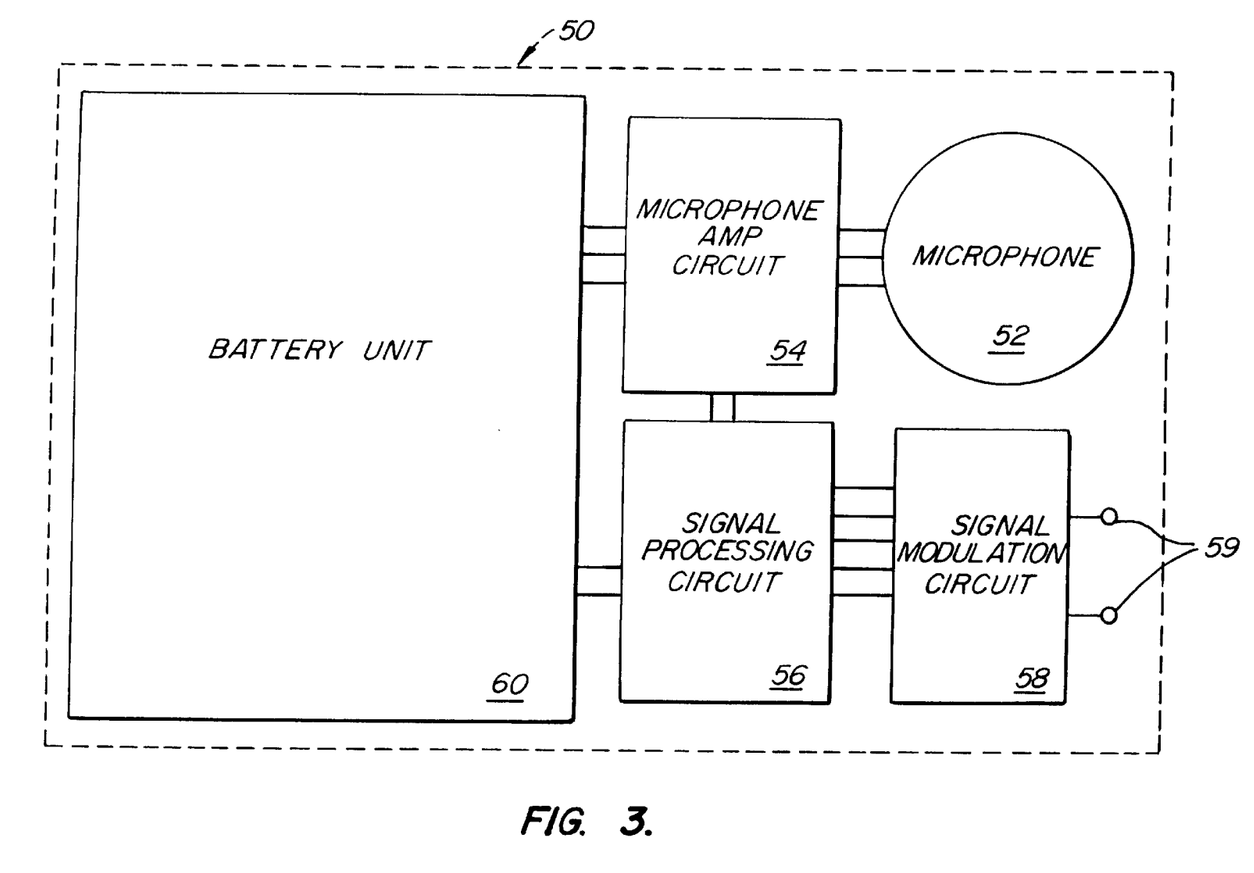
FIG. 3 shows a block diagram of the integrated circuit of the audio processor.

FIG. 3 shows a block diagram of the integrated circuit of the audio processor. An audio processor circuit 50 includes a microphone 52, amplifier circuit 54, signal processing circuit 56, signal modulation circuit 58, and battery 60. The microphone receives ambient sounds and translates the audio sounds into electronic signals. The microphone may be an small electret-type microphone or any other small microphone type.

The electronic signals from the microphone are transmitted to amplifier circuit 54 which amplifies the output from the microphone. Signal processing circuit 56 receives an amplified electronic signal from the amplifier circuit and modifies the signal to best suit the person's hearing abilities. Different signal processing circuits may be manufactured to provide outputs for different kinds of hearing loss. For example, one signal processing circuit may be designed for persons with a mild sloping loss while another circuit may be designed for people with a moderately severe flat hearing loss. Any number of signal processing technologies may be utilized including digital signal processing.

Signal modulation circuit 58 receives a processed electronic circuit from the signal processing circuit and modulates the signal in order to reduce the opportunity for outside electrical interference. Any number of modulation schemes may be utilized including FM and AM types. A modulated electronic signal is delivered to output terminals 59. Battery 60 delivers power to the amplifier circuit, signal processing circuit, and signal modulation circuit. Depending on the type of microphone utilized, the battery may also provide power to microphone 52. In a preferred embodiment, the battery is a small disposable or nonreplacable cell that delivers low power levels to the audio processor circuit (e.g., less than 3 milliamps).

Figure 4:
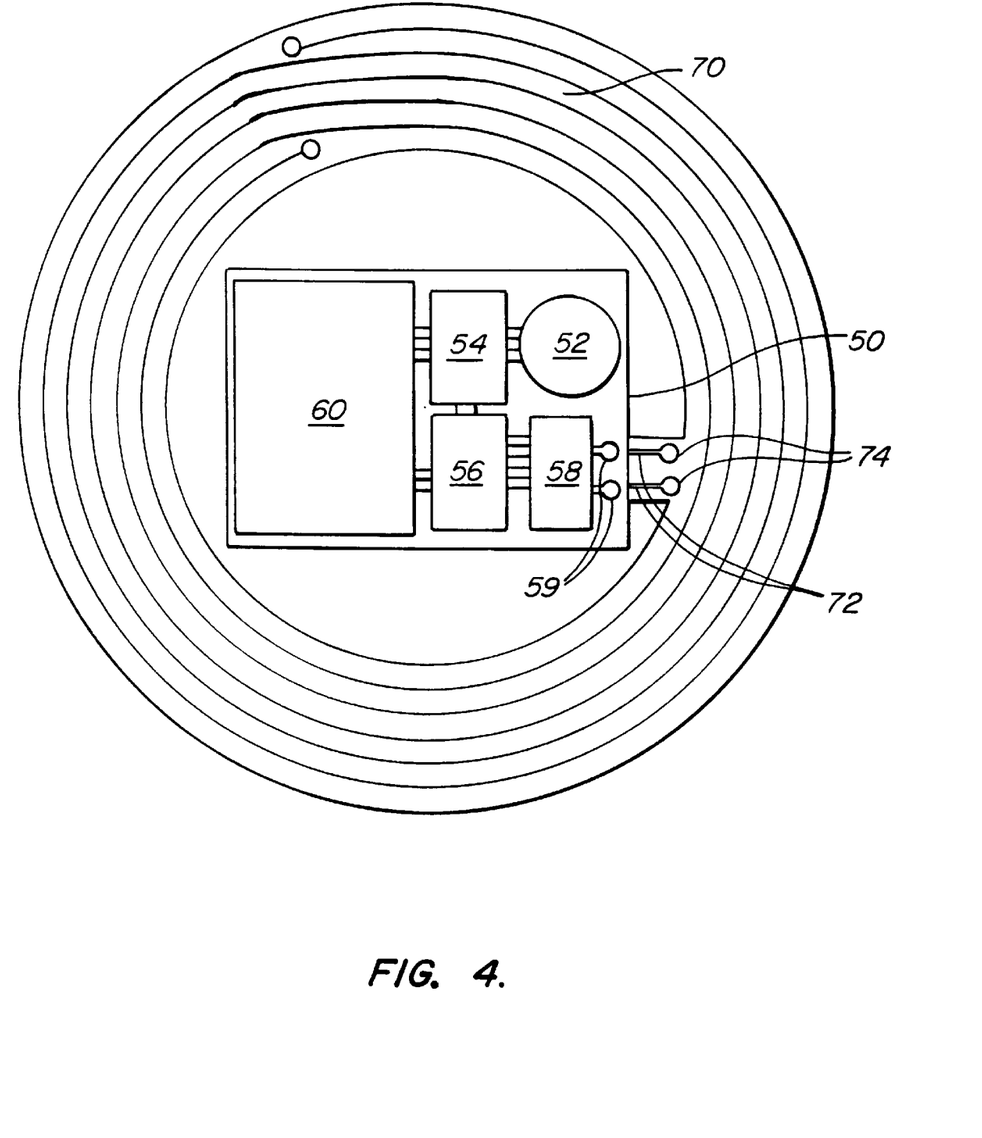
FIG. 4 shows a top view of an embodiment of the audio processor.

FIG. 4 shows a top view of an embodiment of the audio processor circuitry. As shown, the audio processor circuit of FIG. 3 is placed within a coil 70. However, as will be shown in FIG. 5, the audio processor circuit is preferably not in the same plane of the coil. The modulated electronic signal is delivered to output terminals 59 which are electrically connected to the coil. Leads 72 electrically connect output terminals 59 to coil terminals 74 which are each connected to one end of the coil. When electronic signals flow through the coil, the electromagnetic fields generated are utilized to transmit the modulated electronic signal transcutaneously to a receiver located underneath the skin.

Figure 5:
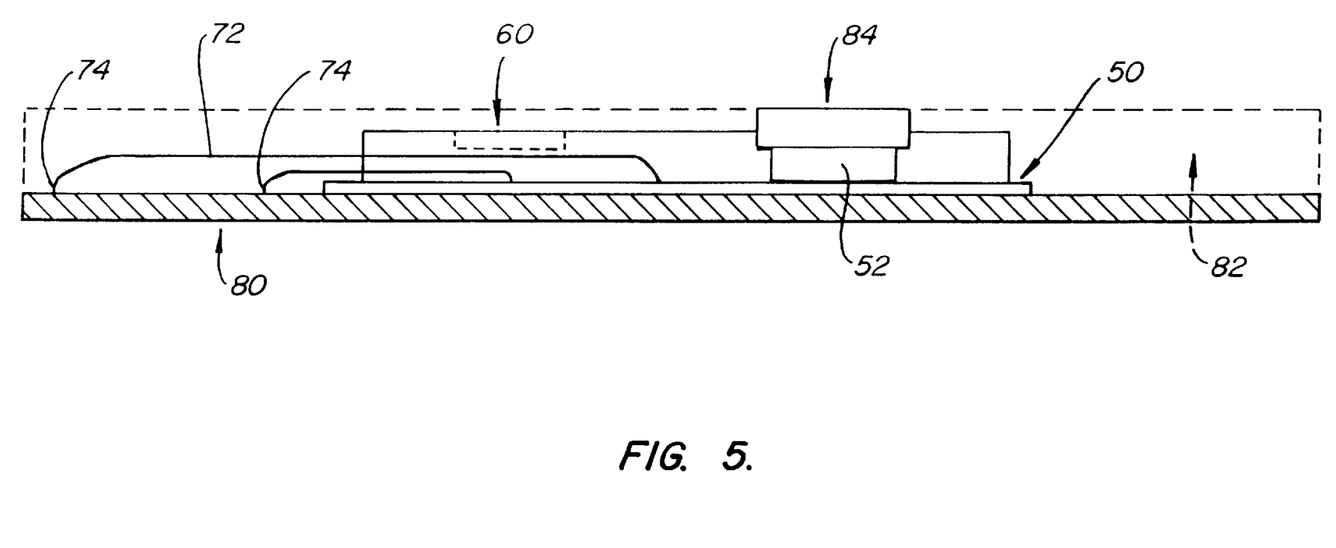
FIG. 5 shows a side view of the audio processor of FIG. 4.

FIG. 5 shows a side view of the audio processor of FIG. 4. The audio processor circuit and coil are mounted on a printed circuit board 80. The audio processor circuit is preferably located outside the plane of the coil so that the electronics do not act as a short in the coil. A microphone port 84 directs sounds to microphone 52 which is incorporated into the audio processor circuit. The audio processor is housed in an epoxy or polymer mold material 82 that is generally impervious to moisture and which imparts mechanical strength to the electronics.

Figure 6:
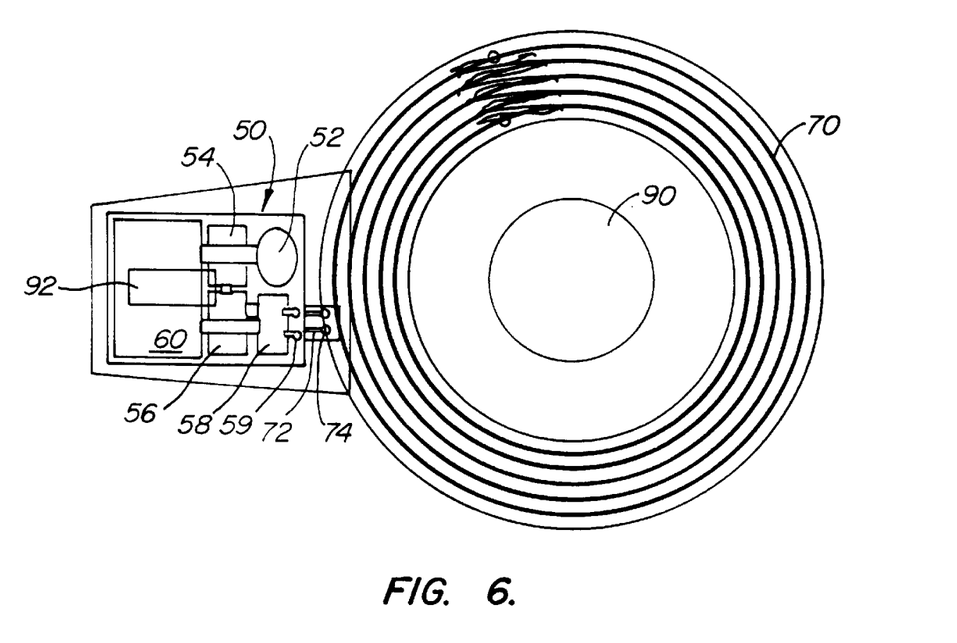
FIG. 6 shows a top view of another embodiment of the audio processor.

FIG. 6 shows a top view of a preferred embodiment of the audio processing circuitry. As shown, the audio processor circuit of FIG. 3 is placed outside the coil. Placing audio processor circuit 50 outside coil 70 prevents the audio processor circuit from shorting out the coil. Within the coil is a magnet 90 that is used to hold the audio processor against the skin and align the audio processor with a transcutaneous receiver. Additionally, an adhesive may be utilized to hold the audio processor against the skin.

Battery 60 employs an on/off switch to ensure that the battery is not drained before the disposable audio processor is to be used. In a preferred embodiment, the battery is a zinc air cell that includes a tape 92 that prevents air from reaching the battery, thus not allowing discharge. When ready for use, the tape is removed allowing air to reach the battery and discharge chemistry occurs. Other on/off switches may be a magnetic switch that is turned on when the audio processor is removed from its container (and its accompanying magnetic field), a grenade pin style contact that is removed to activate the battery, a standard on/off switch, and the like.

Figure 7:
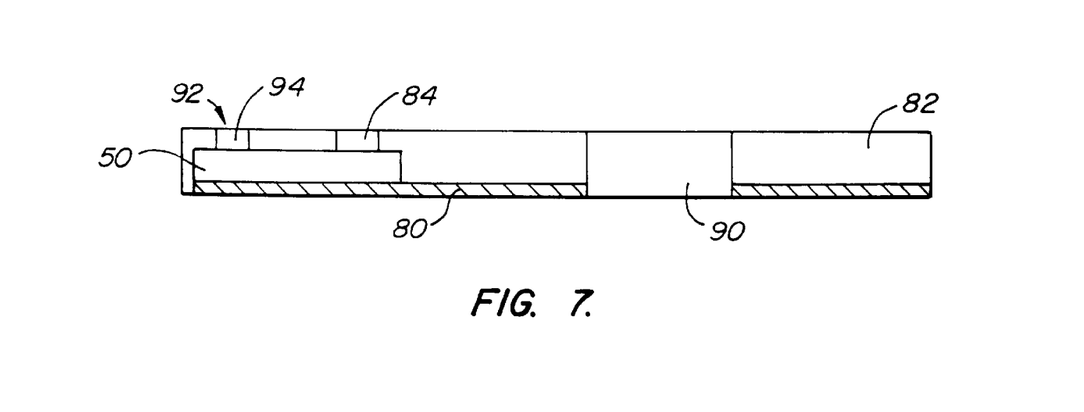
FIG. 7 shows a side view of the audio processor of FIG. 6.

FIG. 7 shows a side view of the audio processor of FIG. 6. Audio processor circuit 50 including the battery are mounted on a printed circuit board 80. Magnet 90 is placed in a hole in the printed circuit board. Epoxy or polymer mold material 82 houses the device with apertures for microphone port 84 and an access 94 to the battery which is covered by tape 92 when the audio processor is not in use.

Figure 8:
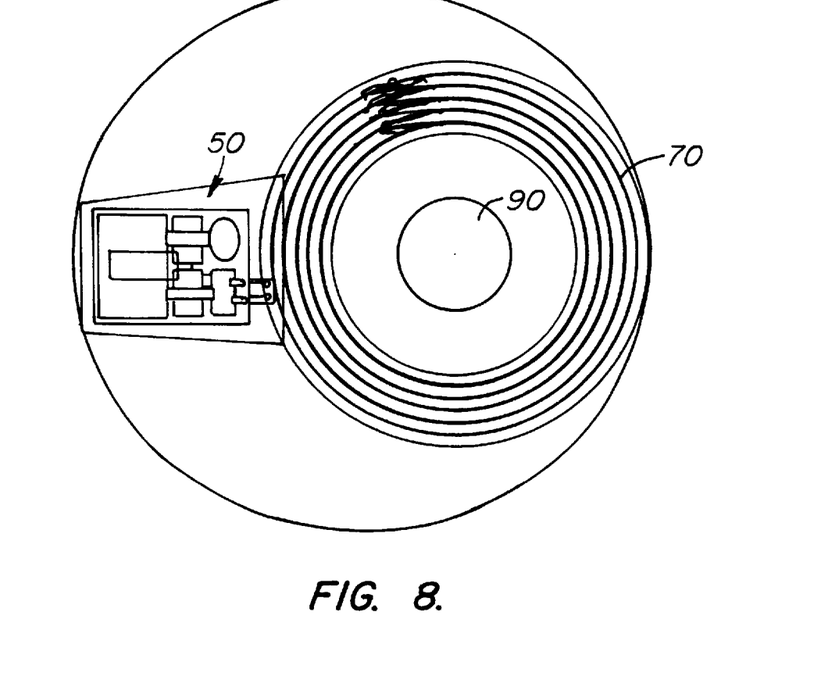
FIG. 8 shows another top view of the audio processor of FIG. 6.

FIG. 8 shows another top view of the audio processor of FIG. 6. Placement of the audio processor circuit outside the coil reduces the overall size of the coil with respect to the audio processor. However, this embodiment provides good isolation between audio processor circuit 50 and coil 70.

Figure 9:
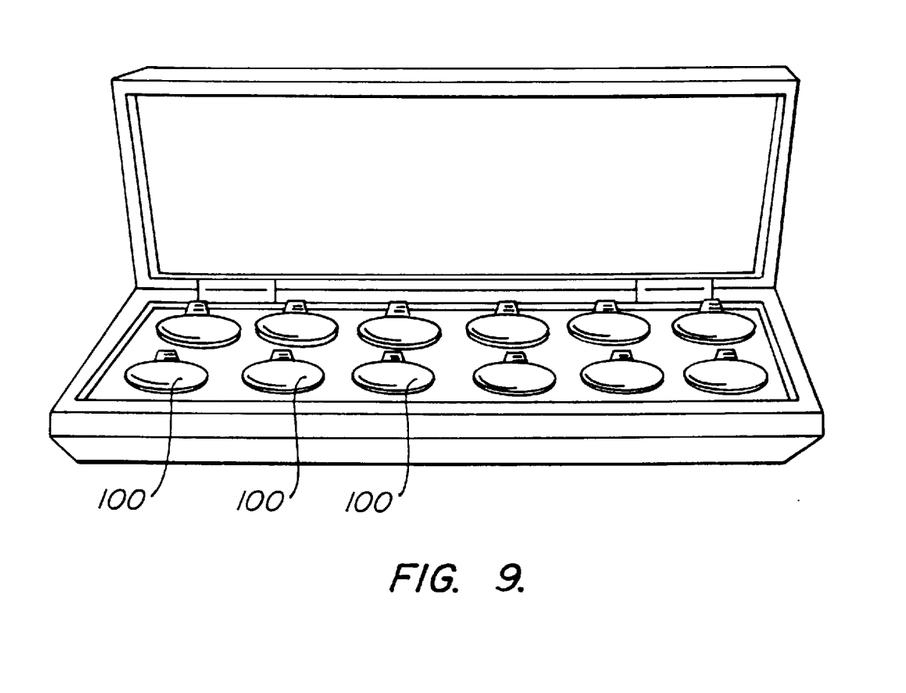
FIG. 9 illustrates a container that houses twelve audio processors of the present invention.

FIG. 9 shows a container that holds 12 disposable audio processors. The audio processor of the present invention provides many advantages over conventional hearing devices. In a preferred embodiment, the audio processors are entirely solid state so there is no need for maintenance. Additionally, the audio processors are low power devices and may be manufactured relatively inexpensively. If an audio processor becomes inoperable because of a malfunction or a low battery, the user simply replaces the audio processor with a new device that is activated when needed. Each audio processor 100 in the container 102 may be designed to best suit the hearing abilities of the hearing impaired person. It is anticipated that the container would supply a hearing impaired person with a full year of maintenance free hearing assistance.

Figure 10:
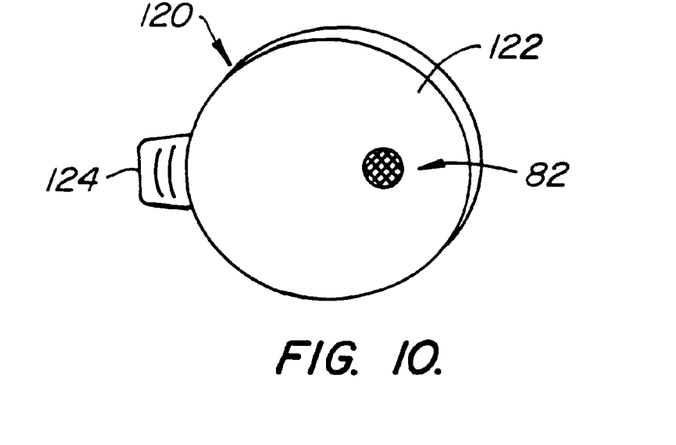
FIG. 10 shows the outer housing of the audio processor.

FIG. 10 shows a top view of an audio processor. An audio processor 120 includes a flexible outer housing 122. The housing may be composed of low cost epoxy, polymer mold, or any other similar material. The housing covers the audio processor circuitry and coil. A tab 124 allows a person to easily manipulate the audio processor to place the audio processor on the skin or remove it therefrom.

Figure 11A:
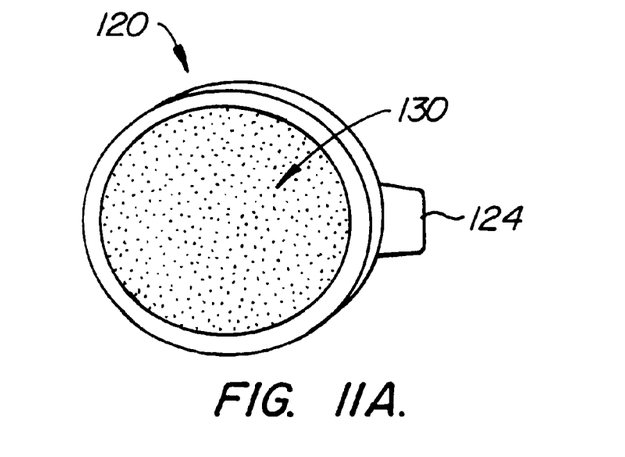
FIGS. 11A and 11B show alternative mechanisms for attaching the audio processor to the skin of a hearing impaired person.
Figure 11B:
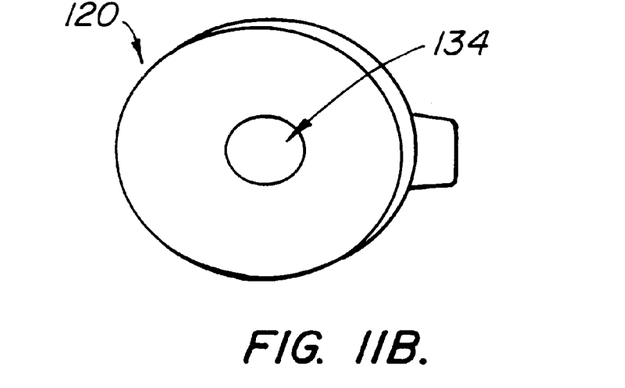

FIGS. 11A and 11B show bottom views of audio processors in order to show different attachment mechanisms. In FIG. 11A, audio processor 120 includes an adhesive back 130. In a preferred embodiment, the adhesive back is also porous to reduce seat accumulation and skin irritation.

In FIG. 11B, audio processor 120 includes a magnet 134 which is utilized to hold the audio processor against the skin of the hearing impaired person because of a magnetic attraction to a magnet implanted under the skin (not shown). In a preferred embodiment, the backing of the audio processor is also porous.

While the above is a complete description of preferred embodiments of the present invention, various alternatives, modifications, and equivalents may be used. It should be evident that the present invention is equally applicable making appropriate modifications to the embodiments described above. Therefore, the above description should not be taken as limiting the scope of the invention which is defined by the metes and bounds of the appended claims.

What is claimed is:

1. A disposable external audio processor for an implantable hearing device, comprising:

a microphone, the microphone producing a electronic signal in response to ambient sounds;

a signal processing circuit coupled to said microphone, the signal processing circuit comprising essentially of a single monolithic application specific integrated circuit which is nonproprammable and specifically designed for one particular category of hearing loss selected from the group consisting of flat, sloping, and midrange deficiency;

a signal modulation circuit coupled to the signal processing circuit, the signal modulation circuit modulating the modified electronic signal;

a coil coupled to the signal modulation circuit, the coil receiving the modulated electronic signal to transmit the modulated electronic signal to the implantable hearing device; and a battery coupled to the signal processing and modulation circuits.

2. The audio processor of claim 1, wherein the signal processing and signal modulation circuits are within a plane of the coil and outside the coil.

3. The audio processor of claim 1, wherein the signal processing and signal modulation circuits are outside the plane of the coil.

4. The audio processor of claim 1, further comprising an amplifier circuit coupled between the microphone and the signal processing circuit, the amplifier circuit amplifying the electronic signal.

5. The audio processor of claim 1, further comprising a housing encompassing the microphone, the signal processing circuit, the signal modulation circuit, the coil and the battery, the housing being composed of epoxy or polymer mold material wherein the housing includes a tab, whereby a person may handle the audio processor by grasping the tab.

6. The audio processor of claim 1, wherein the battery provides less than 3 milliamps of power during operation of the audio processor.

7. The audio processor of claim 1, wherein the battery is nonreplaceable.

8. A system comprising a container, the container holding a plurality of disposable external audio processors each of the audio processors comprising:

a microphone, the microphone producing a electronic signal in response to ambient sounds;

a signal processing circuit coupled to said microphone, the signal processing circuit comprising essentially of a single monolithic application specific integrated circuit which is nonprogrammable and specifically designed for one particular category of hearing loss selected from the group consisting of flat, sloping, and midrange deficiency;

a signal modulation circuit coupled to the signal processing circuit, the signal modulation circuit modulating the modified electronic signal;

a coil coupled to the signal modulation circuit, the coil receiving the modulated electronic signal to transmit the modulated electronic signal to the implantable hearing device; and a battery coupled to the signal processing and modulation circuits.

9. A system as in claim 8, wherein the audio processors are all pre-programmed identically.

\* \* \* \* \*